United States Patent [19]

Scirica et al.

[11] Patent Number: 5,733,293
[45] Date of Patent: Mar. 31, 1998

[54] DISPOSABLE LOADING UNIT FOR A VASCULAR SUTURING INSTRUMENT

[75] Inventors: Paul A. Scirica, Huntington; David M. Farascioni, Danbury; Corbett W. Stone, Newtown, all of Conn.

[73] Assignee: United States Surgical Corporation, Norwalk, Conn.

[21] Appl. No.: 646,613

[22] Filed: May 8, 1996

[51] Int. Cl.⁶ .................................................. A61B 17/04
[52] U.S. Cl. ........................ 606/144; 206/63.3; 206/339
[58] Field of Search ................... 606/144; 206/63.3, 206/339, 340, 341; 221/2

[56] References Cited

U.S. PATENT DOCUMENTS

| | | |
|---|---|---|
| 3,456,817 | 7/1969 | Irazoqui . |
| 3,613,901 | 10/1971 | Montelius . |
| 3,901,244 | 8/1975 | Schweizer . |
| 4,084,692 | 4/1978 | Bilweis . |
| 4,116,333 | 9/1978 | Pavel . |
| 4,135,623 | 1/1979 | Thyen . |
| 4,183,431 | 1/1980 | Schmidt et al. . |
| 4,418,821 | 12/1983 | Sandel . |
| 4,424,898 | 1/1984 | Thyen et al. . |
| 4,449,630 | 5/1984 | Filhol . |
| 4,496,045 | 1/1985 | Ferguson et al. . |
| 4,524,891 | 6/1985 | Silva . |
| 4,821,878 | 4/1989 | Jones . |
| 5,056,658 | 10/1991 | Sobel et al. . |
| 5,078,730 | 1/1992 | Li et al. . |
| 5,086,914 | 2/1992 | Mish et al. . |
| 5,152,422 | 10/1992 | Springer . |
| 5,199,565 | 4/1993 | Voroba . |
| 5,226,536 | 7/1993 | Elliott . |
| 5,271,495 | 12/1993 | Alpern . |
| 5,478,344 | 12/1995 | Stone et al. . |
| 5,478,345 | 12/1995 | Stone et al. . |

FOREIGN PATENT DOCUMENTS

| | | |
|---|---|---|
| 0647431 | 4/1995 | European Pat. Off. . |
| 2260704 | 4/1993 | United Kingdom . |

*Primary Examiner*—Gary Jackson

[57] ABSTRACT

A loading unit is provided for use with a surgical vascular suturing instrument. The loading unit is dimensioned and configured to securely retain a surgical needle and an associated length of suture in a position to be received by a jaw of the vascular suturing instrument. The loading unit generally includes one or more needle supply stations each of which include needle support structure and jaw receiving structure. The needle supporting structure releasably secures a surgical needle to the loading unit and the jaw receiving structure is dimensioned and configured to guide the jaw of a vascular suturing instrument about an end of the surgical needle. The needle supply station also includes a shield to protect the pointed end of the surgical needle during storage and transportation. The loading unit also includes suture retaining structure for holding the length of suture material attached to the surgical needle.

24 Claims, 8 Drawing Sheets

FIG_10

DISPOSABLE LOADING UNIT FOR A VASCULAR SUTURING INSTRUMENT

BACKGROUND

1. Technical Field

This device relates generally to surgical suturing instrumentation and, more particularly, to a loading unit for supplying surgical needles and associated sutures to a surgical vascular suturing instrument.

2. Background of Related Art

Various types and styles of suture packages have been developed to hold surgical needles and associated lengths of suture for use during a surgical operation. These devices typically include a folded pouch containing a single needle and suture combination. To access the needle and suture, the package is unfolded and the needle/suture is removed by hand. During many surgical procedures, it is generally considered desirable to place two or three lines of stitching in tissue sections, such as, for example, to provide reinforcement when performing an anastomosis. A device for holding a plurality of sutures and needles is disclosed in U.S. Pat. No. 4,185,636 to Gabbay et al. Gabbay et al. disclose annular organizer members for holding multiple sutures each having a needle attached at one end thereof. Another device for holding several needles and sutures is disclosed in U.S. Pat. No. 4,424,898 to Thyen et al. The device of Thyen et al. includes a plurality of holders for surgical needles and a channel around the outer perimeter of the device to hold the sutures associated with the needles.

In using these various suture packages, it is often necessary to manually remove the needle/suture combination by hand and insert them into a surgical suturing apparatus. A dispenser for holding surgical needles and anchors is disclosed in U.S. Pat. No. 4,821,878 to Jones. The Jones dispenser is configured to hold the anchors in a position to be grasped by a manipulating tool.

During many surgical procedures it is desirable to remotely join tissue together by passing a needle, having a length of suture material attached thereto, back and forth through tissue and between the jaws of a suturing instrument which are positioned on opposite sides of the tissues. This procedure was traditionally accomplished by hand. One such instrument, along with a loading unit for positioning a surgical incision member within the jaws of the instrument, is disclosed in U.S. Pat. No. 5,478,344. The suturing instrument disclosed therein receives the pointed ends of the surgical incision member within a recess located in each of the jaws. The loading unit requires that the pointed ends of the needle be contained within both jaws prior to removal.

An alternative loading unit is disclosed in U.S. Pat. No. 5,478,345 and includes provision for retaining multiple needle-suture combinations.

One other exemplary suturing instrument is a vascular suturing instrument disclosed in U.S. patent application Ser. No. 08/352,908. This particular instrument is preferably loaded by positioning a single U-shaped jaw of the vascular suturing instrument about a suture retaining end of a surgical needle and retracting a clamping member to hold the needle within the jaw.

Thus, during many surgical procedures, it is necessary to rapidly and accurately place successive needle-suture combinations within a single jaw of a surgical vascular suturing instrument for immediate and repeated use during the surgical procedure. Further, it is often necessary to grasp the needle at a specific location along the needle body to facilitate loading and suturing, such as, for example, at a suture retaining end of the surgical needle. Thus, it is desirable to have a needle and suture supplying device or loading unit which is capable of supplying one or more needle-suture combinations and positioning them within a single jaw of a surgical vascular suturing instrument. It is also desirable to have an instrument receiving structure associated with the device for receipt of a single jaw of a surgical vascular suturing instrument and to guide the jaw into position for precisely grasping an end of a needle within the jaw of the vascular suturing instrument.

SUMMARY

There is provided a loading unit for use with a surgical vascular suturing instrument. The loading unit is dimensioned and configured to securely support a surgical needle and associated length of suture material in a position to be grasped by a single jaw of the vascular suturing instrument. Each needle supply station includes needle support structure and jaw receiving structure. The loading unit may additionally include suture retaining structure.

The needle support structure preferably includes a relatively inflexible leg having a notch thereon for supporting a first portion of the surgical needle and at least one, and preferably two, relatively flexible legs for engaging and biasing the surgical needle within the notch at second and third portions of the surgical needle.

The jaw receiving structure preferably includes a relatively straight first arm which may be integrally formed with the inflexible leg and a generally L-shaped second arm spaced apart from the first arm. Each of the first and second arms may be provided with lips along an edge thereof to releasably secure the jaw of the vascular suturing instrument between the arms. Preferably, the L-shaped arm has a notch through which a portion of the suture may extend. Further, the L-shaped arm includes an angled portion which engages a wide portion of the jaw of the vascular suturing instrument and serves to limit the advancement of the vascular suturing instrument between the arms thereby precisely positioning the clamping end of the jaw about a suture end of the surgical needle. Angled surfaces are provided on each of the inflexible leg and on portions of the L-shaped second arm to facilitate removal and withdrawal of the surgical needle from the needle supply station. Preferably, the needle supply station also includes structure to protect the pointed end of the surgical needle. This structure is preferably in the form of a U-shaped trough or shield which protects the user and the point of the surgical needle during storage and transportation.

The base of the loading unit preferably includes a top plate and a bottom plate which together define a cavity therebetween. The top plate includes an opening which is communicable with the cavity. Preferably, suture retaining structure in the form of a suture rail is located within the cavity. The suture may extend from the suture end of the surgical needle through the suture notch of the second arm and through the opening. The suture is wound about the suture rail. Preferably, the loading unit is provided with two needle supply stations positioned at opposite ends of the generally oval shaped base. Each needle supply station faces in an opposite direction. Thus, when the loading unit is grasped by the hand of the user it may be rotated to the second needle supply station which will point in the proper direction for ease of insertion of a vascular suturing instrument.

A method of applying the surgical needle to the suturing instrument utilizing the aforedescribed loading unit is also provided.

BRIEF DESCRIPTION OF THE DRAWINGS

Various embodiments are described herein with reference to the drawings, wherein.

DETAILED DESCRIPTION OF PREFERRED EMBODIMENTS

Figures 1, 2:
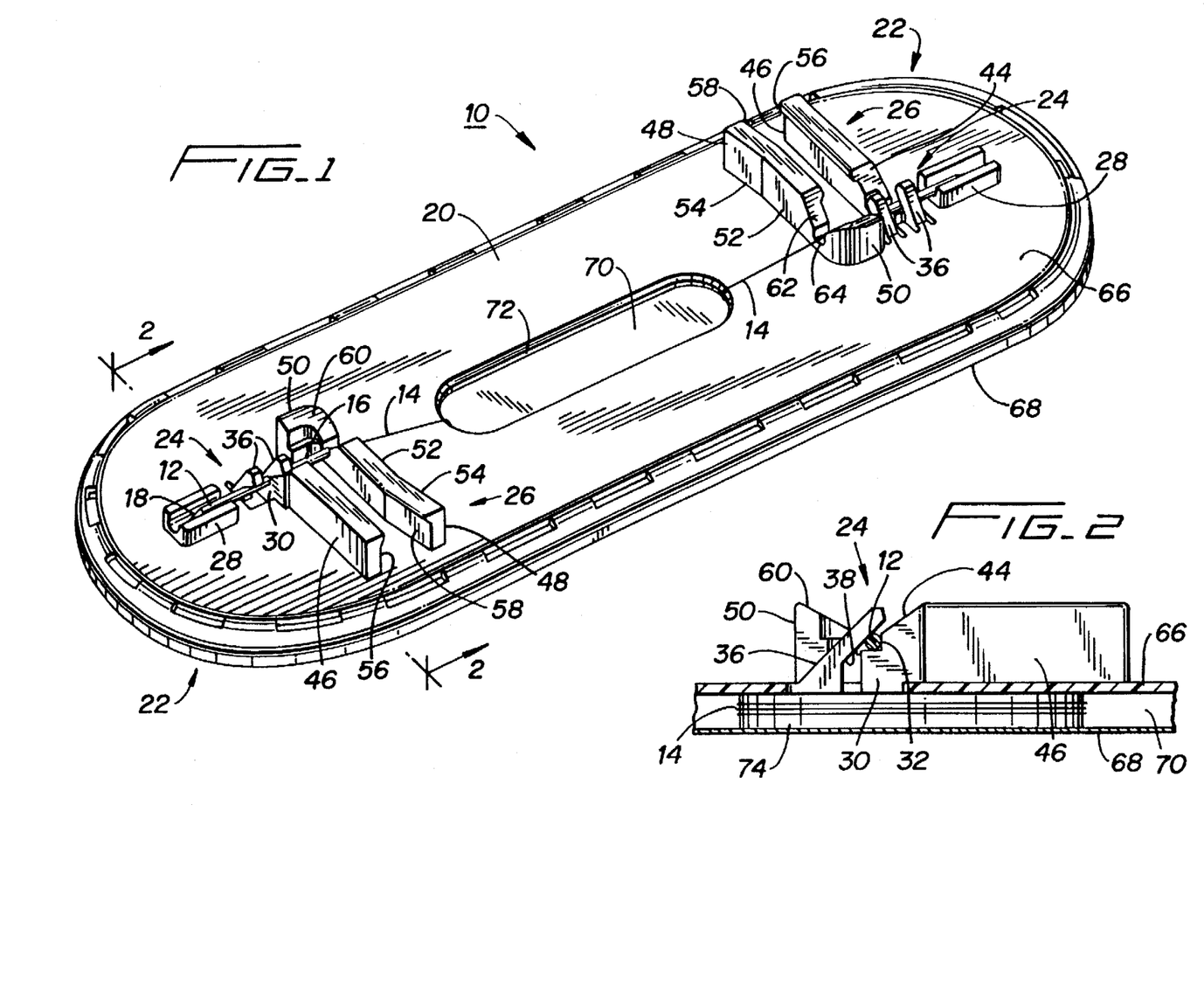
FIG. 1 is a top perspective view of a preferred embodiment of a disposable loading unit.
FIG. 2 is a sectional view taken along the line 2—2 of FIG. 1.

With reference to FIG. 1, there is illustrated a preferred embodiment of a loading unit 10 which is configured to supply at least one surgical needle 12 and an attached length of suture 14 for positioning within the jaw of a vascular suturing instrument. Preferably surgical needle 12 is of the type having suture 14 attached at a suture end 16 of needle 12 and having a pointed tip or end 18 opposite thereof. It should be noted that, while the following disclosure is provided with reference to a single pointed surgical needle having a suture attached at one end thereof, it is within the contemplated scope of the present disclosure that various other needle configurations, such as, for example, curved needles, or needles having points at both ends with a suture attached intermediate the points, may be provided on loading unit 10 to facilitate supplying to and grasping by various suturing instruments. Also a double armed suture, e.g. a needle at both ends of the suture can be provided.

Loading unit 10, preferably disposable, includes a base or body portion 20 having one or more needle supply stations 22 positioned thereon. Preferably there are provided two needle supply stations 22, one at each end of loading unit 10 and each facing in an opposite direction. Clearly, a fewer or larger number of supply stations could be provided. Each needle supply station 22 includes needle support structure 24 for securely holding needle 12 above base 20 and jaw receiving structure 26 configured to receive and guide a single jaw of a vascular suturing instrument in a direction generally orthogonal to needle 12 and position the jaw about suture end 16 of surgical needle 12 in the manner described in more detail hereinbelow. Additionally, each needle supply station 22 may also include a U-shaped trough or shield 28 which is configured to surround and protect pointed end 18 of surgical needle 12 when surgical needle is retained within needle support structure 24. Shield 28 significantly reduces the chance of injury to a user and aids in preventing damage to the pointed end of surgical needle 12. Further, the generally U-shape of shield 28 allows surgical needle 12 to be lifted clear of loading unit 10 without damaging pointed end 18.

Figure 3:
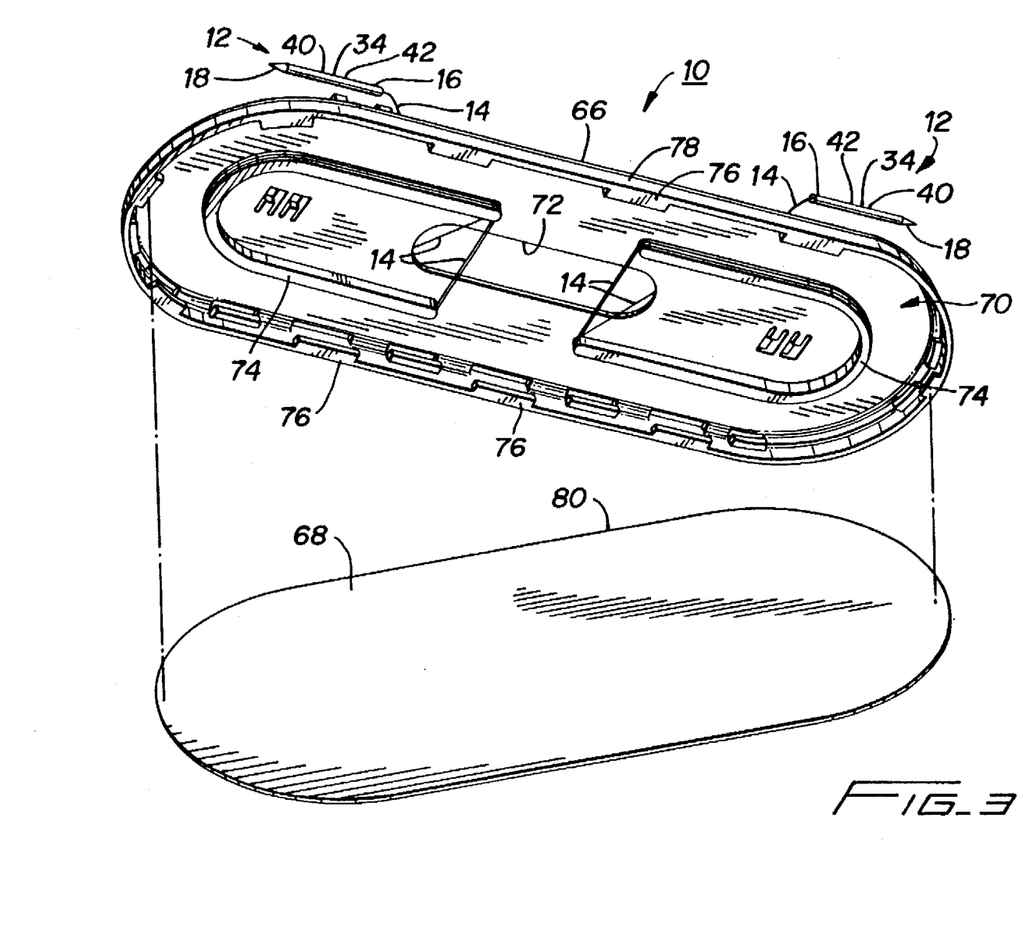
FIG. 3 is a bottom perspective view, with parts separated, of the embodiment of FIG. 1.

Referring to FIGS. 1, 2 and 3, needle support structure 24 includes a single relatively inflexible support leg 30 having a notch 32 (FIG. 2) thereon. Notch 32 is configured to engage and support surgical needle 12 at a first portion 34 (See FIG. 3) thereof. These potions are clearly illustrated in FIG. 3 wherein surgical needle 12 is shown detached from loading unit 10 to identify the specific potions of needle 12 engaged by needle support structure 24. Each needle support structure 24 preferably further includes two flexible legs 36 each having a contacting surface 38 for engaging surgical needle 12 at second and third potions, 40 and 42, (FIG. 3) respectively. Flexible legs 36 firmly engage and hold surgical needle 12 against notch 32 and yet are sufficiently resilient or flexible so as to allow surgical needle 12 to be lifted clear of the needle support structure 24. An inclined surface 44 on support leg 30 facilitates withdrawal of surgical needle 12 from needle support structure 24.

Referring specifically to FIG. 1, and as noted above, jaw receiving structure 26 is provided to securely and precisely align a single jaw of a vascular suturing instrument in position about suture end 16 of surgical needle 12. Jaw receiving structure 26 includes a relatively straight first arm 46 and a generally L-shaped second arm 48 spaced apart from first arm 46. First arm 46 and second arm 48 are configured to position a jaw of a vascular suturing instrument therebetween. First and second arms, 46 and 48, respectively, are oriented on the base in a direction generally perpendicular to needle 12 so as to guide the jaw of the vascular suturing instrument in a direction generally orthogonal to needle 12. Second arm 48 includes a stop potion 50 and a straight potion 52 extending generally at a right angle therefrom. An angled potion 54 is provided adjacent straight potion 52. Stop potion 50 in conjunction with angled potion 54 limit the degree of advancement of a jaw of a vascular suturing instrument between first and second arms, 46 and 48, respectively. Additionally, arms 46 and 48 may be provided with lips 56 and 58, respectively, which facilitate securing the jaw of the vascular suturing instrument therebetween. It should be noted that where lips 56 and 58 are provided, first and second arms 46 and 48 are sufficiently flexible to allow the jaw of the vascular suturing instrument to be lifted clear of lips 56 and 58.

An angled surface 60 is provided on stop potion 50 and an angled surface 62 is provided on straight portion 52 to facilitate removal of surgical needle 12 from a needle support structure 24 and allow needle 12 to clear jaw receiving structure 26. Additionally, a suture notch 64 is formed in straight potion 52 and in alignment with suture end 16 of surgical needle 12. Suture notch 64 flows suture 14 to extend directly from suture end 16 into suture receiving structure formed in loading unit 10 which will now be described. Notch 64 also supports the suture end 16 of needle 12 (see FIG. 8).

Referring to FIGS. 1-3, base 20 generally includes a top plate 66 and a bottom plate 68 which together define a cavity 70 therebetween. An opening 72 is formed in top plate 66, preferably intermediate supply stations 22, and allows suture 14 to extend into cavity 70. Base 20 is shown oval shaped, however other configurations are contemplated.

Referring now specifically to FIGS. 2 and 3, a significant portion of the length suture 14 is stored within loading unit 10 inside cavity 70. Suture retaining structure, preferably in the form of a suture rail 74, is provided within cavity 70 and affixed to top plate 66. Suture 14 extends from suture end 16 of needle 12, extends through opening 72 and is wrapped around raft 74. While the illustrated embodiment utilizes a suture rail 74 to retain suture 14, it is within the scope in the present disclosure to provide other suture retaining structure such as, for example, channels formed in top plate 66 or bottom plate 68, or movable structure in the form of suture reels movably mounted within cavity 70.

Figure 3A:
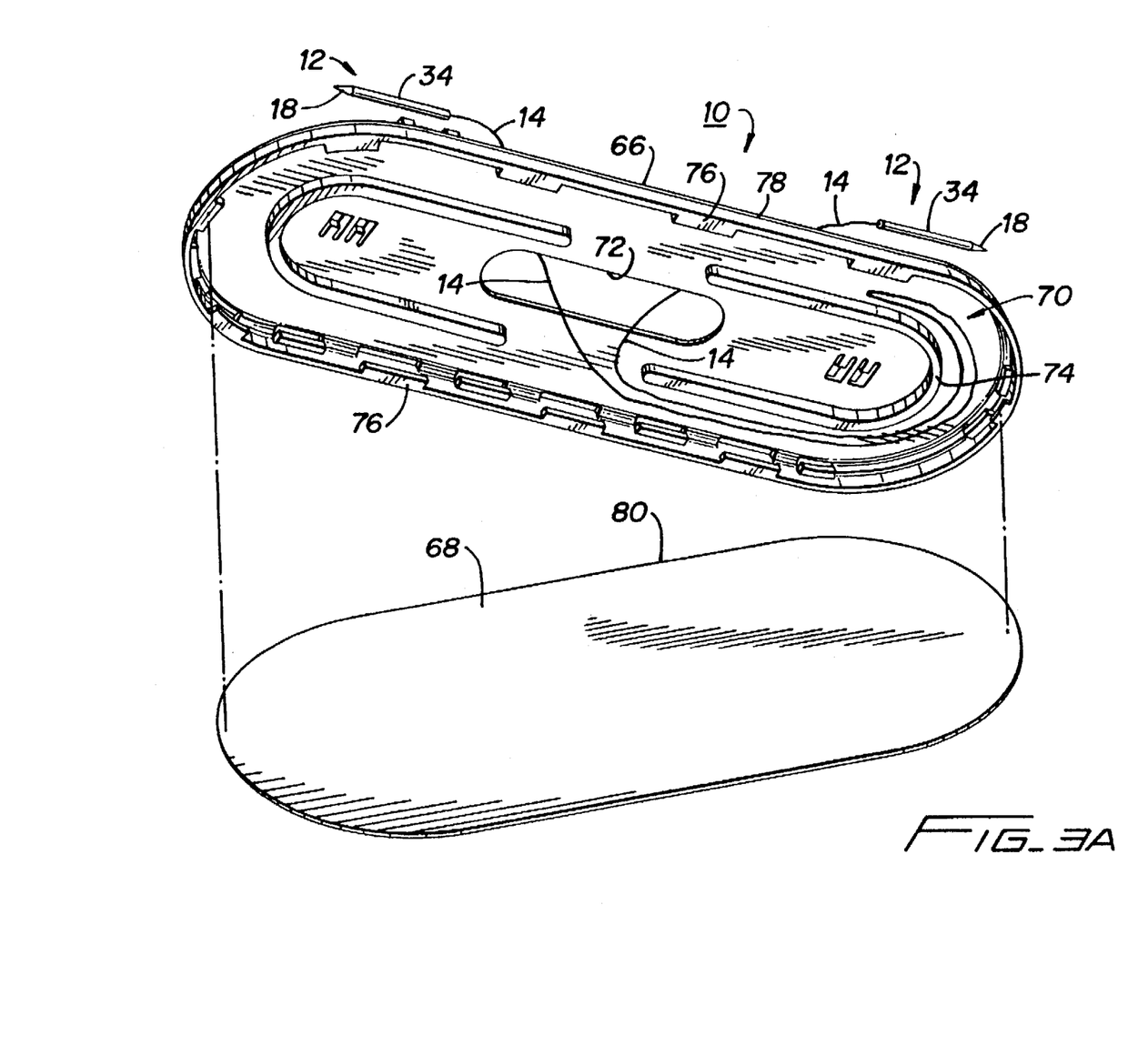
FIG. 3A is a bottom perspective view, with parts separated, of the disposable loading unit of FIG. 1 mounting a double armed suture.

FIG. 3A illustrates a perspective view of the loading unit mounting a double armed suture.

Referring specifically to FIG. 3, bottom plate 68 is detachably affixed to top plate 66 by means of flexible tabs 76 formed along an edge 78 of the top plate 66. An outer edge 80 of bottom plate 68 fits in press or snap fit engagement into flexible tabs 76 to thereby define cavity 70.

Referring now to FIGS. 4–7, there is illustrated a preferred embodiment of a vascular suturing instrument of the type disclosed in U.S. patent application Ser. No. 08/532,908, entitled Vascular Suturing Apparatus, the disclosure of which is incorporated herein by reference. The apparatus of this embodiment provides automatic transfer of the surgical needle between the two jaws, accomplished with a single hand of the user.

Figure 4:
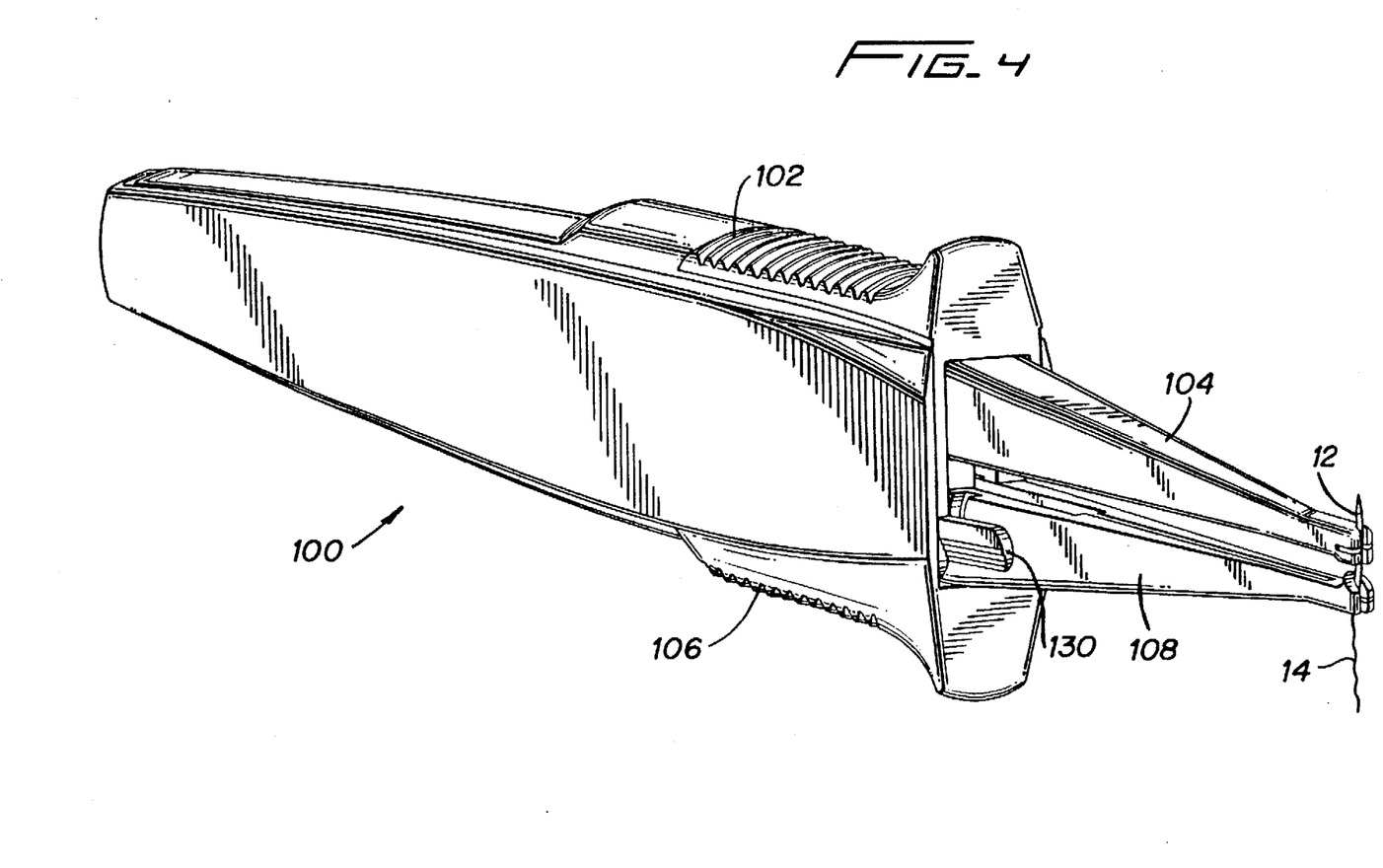
FIG. 4 is a perspective view of one embodiment of a vascular suturing instrument suitable for use within the disposable loading unit of FIG. 1.

With initial reference to FIG. 4, vascular suturing instrument 100 has an upper arm or housing 102 supporting an upper jaw 104 and a lower arm or housing 106 supporting a lower jaw 108. Arms 102, 106 are configured to be gasped by the surgeon in a tweezer-like manner to facilitate control of the apparatus for suturing the tissue. Lower arm 106 and lower jaw 108 remain fixed as upper arm 102 and upper jaw 104 move relative thereto to pass surgical needle 12, with attached suture 14, between jaws 104, 108.

As can be appreciated, the terms "upper" and "lower" as used herein refer to the orientation of the instrument shown in FIG. 4; clearly if the orientation of the instrument changes, these designations will change. Additionally, needle 12 can be straight as shown, although other needle sizes and configurations, such as curved needles, are also contemplated.

Figure 5:
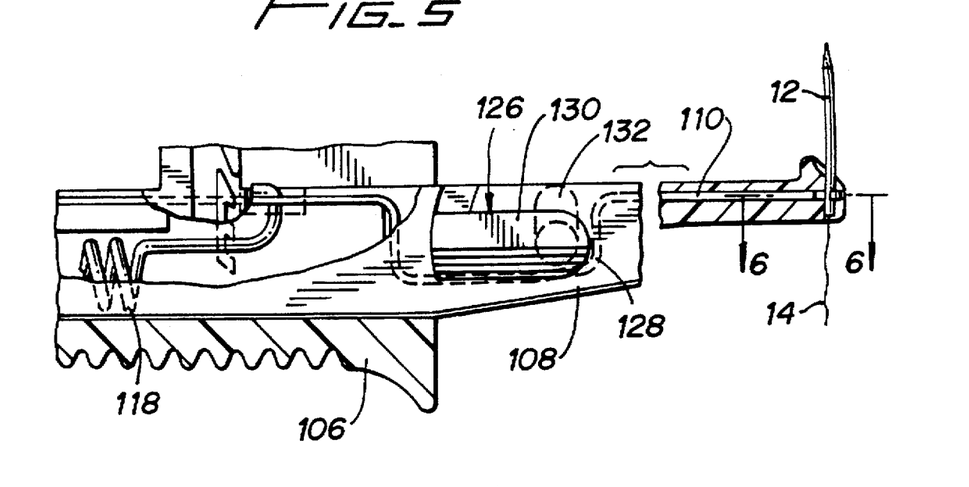
FIG. 5 is an enlarged side view, partially shown in section, of a distal end of a lower jaw of the vascular suturing instrument of FIG. 4.
Figure 6:
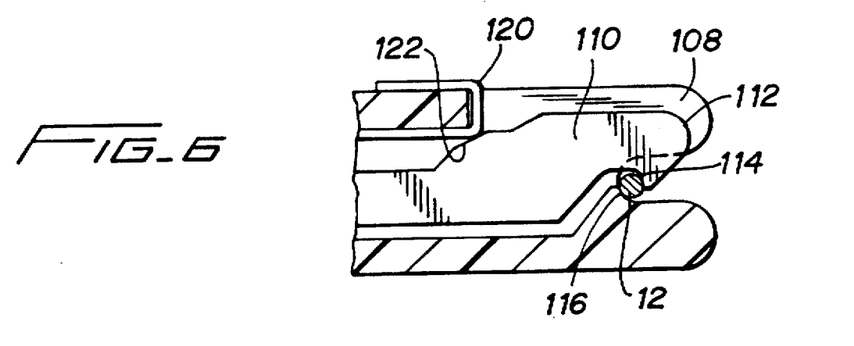
FIG. 6 is an enlarged cross-sectional view taken along line 6—6 of FIG. 5 showing securement of a needle in the lower jaw.

Turning now to FIGS. 5 and 6, the needle securing (clamping) blades of apparatus 100 includes a lower blade 110 slidably mounted within lower jaw 108 for movement between a proximal position for clamping surgical needle 12 and a distal position for releasing surgical needle 12. As used herein, the term "proximal" refers to that portion of the instrument, or component thereof, closer to the user, while the term "distal" refers to that portion of the instrument; or component thereof, further from the user. More specifically, a distal end 112 of lower blade 110 has a recess defined by a locking edge 114 which presses needle 12 against a surface 116 of lower jaw 108 (FIG. 6). When in the proximal clamping position, (FIGS. 5 and 6) a coil spring 118 biases lower blade 110 in a proximal direction such that a biasing clip 120 (or alternately a biasing pin or biasing plate) engages an angled surface 122 of blade 110 to bias it into engagement with needle 12 and to force it against a surface 124 of lower jaw 108 to securely clamp needle 12 between lower blade 110 and lower jaw 108. When in the distal release position (FIG. 7), angled surface 122 is no longer in contact with biasing clip 120 and therefore locking edge 114 no longer presses needle 12 against surface 116 thereby facilitating release of needle 112. An upper blade (not shown) slidably mounted within upper jaw 104 functions in a similar manner.

Figure 7:
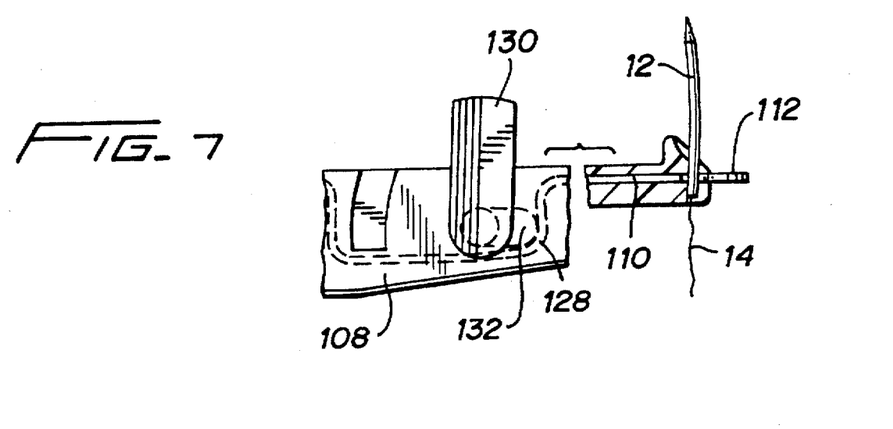
FIG. 7 is an enlarged cross-sectional view of the needle release mechanism.

Vascular suturing instrument 100 includes a quick release mechanism 126 to load or remove and reload surgical needle 12. In the illustrated embodiment, needle 12 needs to be positioned in lower jaw 108 to use the quick release mechanism, however it is also contemplated that the release mechanism can be positioned on upper jaw 104 which would require needle 12 to be in upper jaw 104 in order to be replaced. Referring to FIGS. 5 and 7, a bend 128 is formed in lower blade 110 to cooperate with a release lever 130. As shown in FIGS. 4, 5 and 7, an arm 132 extends from release lever 130 which is mounted in lower jaw 108. To replace needle 12, lever 130 is rotated clockwise, causing arm 132 to contact bend 128 of lower blade 110. This forces blade 110 distally to release needle 12 from jaw 108. With blade 110 in the distal needle release position (see e.g. FIG. 7), needle 12 can be inserted or removed from its position between lower blade 110 and lower jaw 108. As lever 130 is released to return to its initial position of FIGS. 4 and 5, lower blade 110 to returns to the proximal clamping position under the force of coil spring 118.

Figure 8:
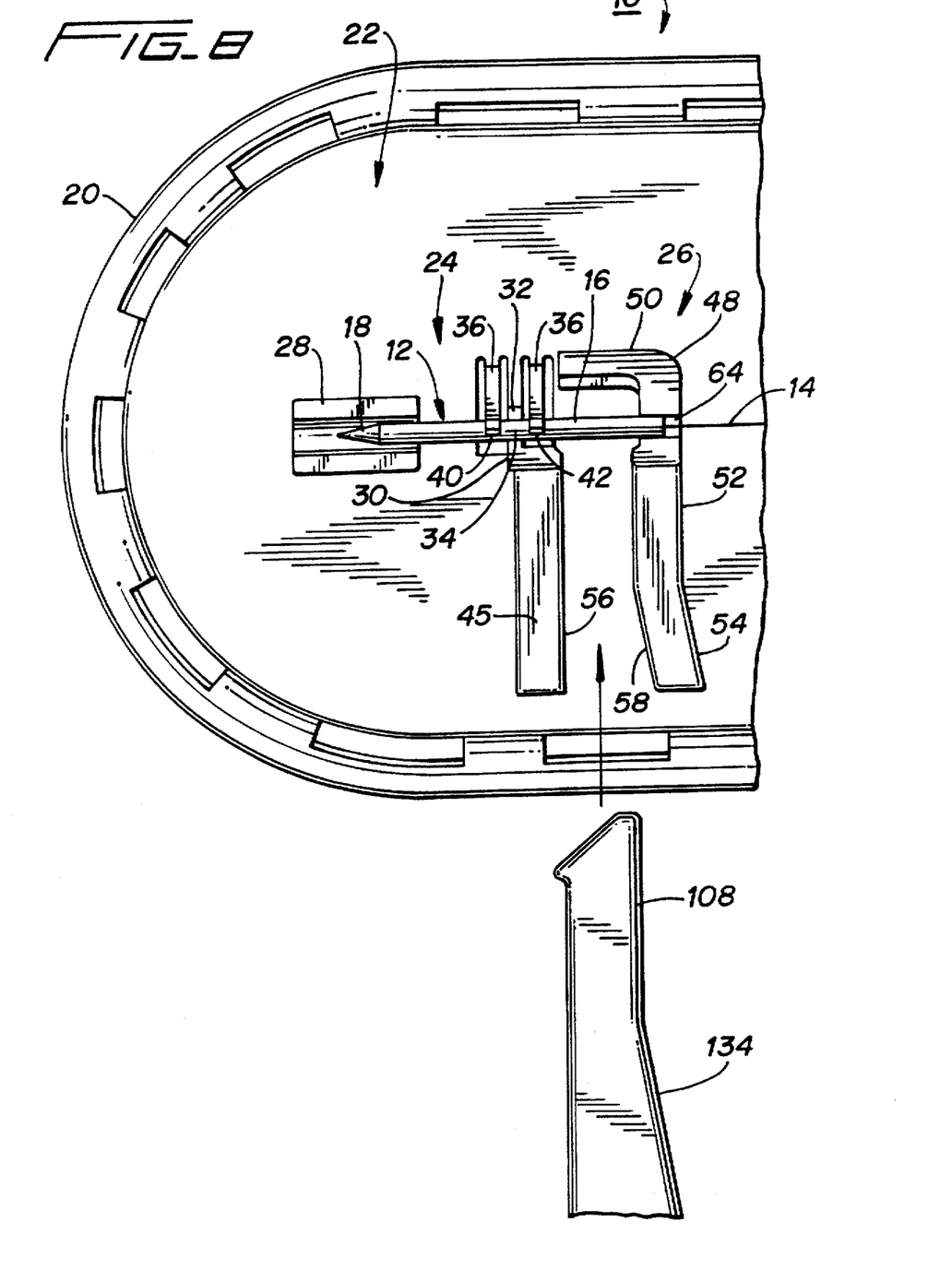
FIG. 8 is a top view showing a portion of the lower jaw of the vascular suturing instrument of FIG. 4 being advanced toward a loading station of the disposable loading unit of FIG. 1.
Figure 9:
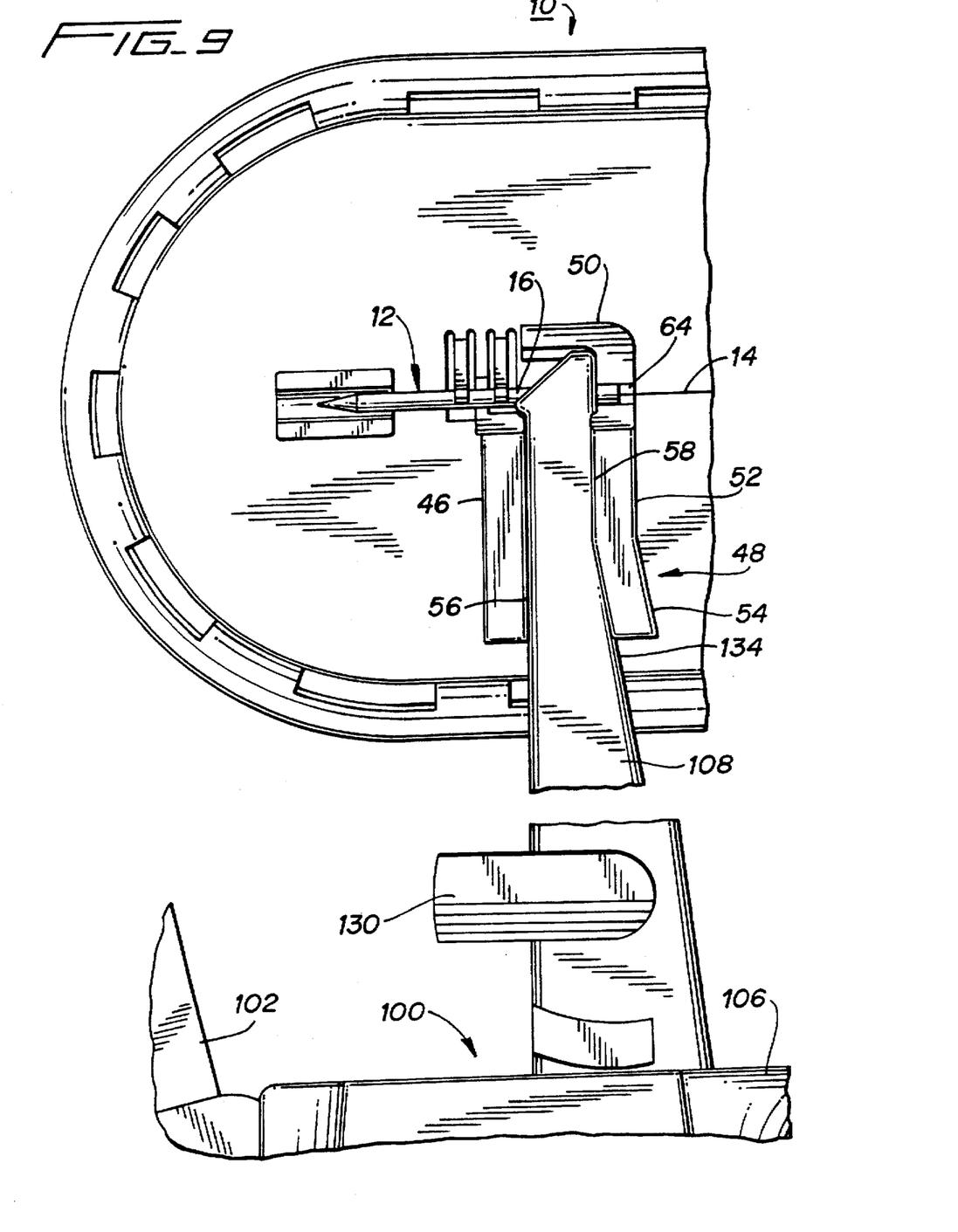
FIG. 9 is a top view showing the lower jaw positioned in the loading station with the needle release mechanism in a needle release position.
Figure 10:
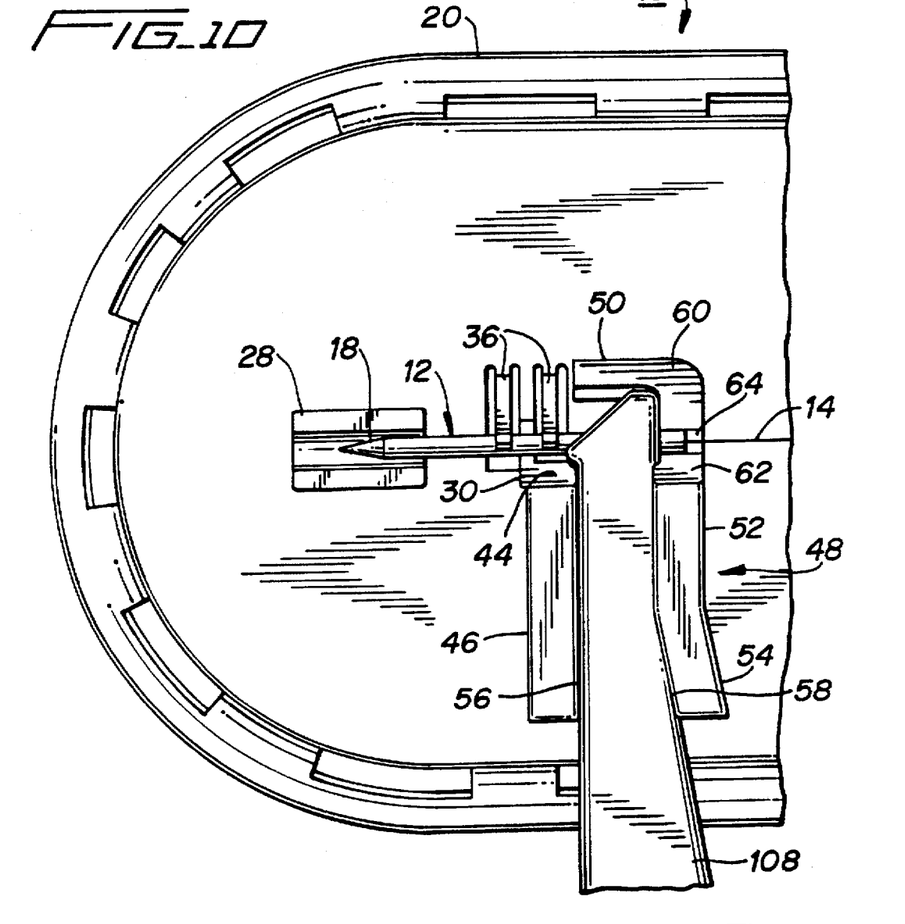
FIG. 10 is a view similar to FIG. 9 with the needle release mechanism in the needle clamping position.

Referring now to FIGS. 8–10, the operation of loading unit 10 to load a surgical needle 12 having a length of suture 14 attached thereto, into a lower jaw 108 of a vascular suturing instrument 100 will now be described. Prior to insertion of lower jaw 108 into jaw receiving structure 26, vascular suturing instrument 100 is manipulated to an open position separating upper arm 102 from lower arm 106. Release lever 130 is moved to an open or needle releasing position as illustrated in FIG. 7 and described above. Thus, vascular suturing instrument 100 is in a condition to receive a surgical needle.

Referring to FIG. 8, surgical needle 12 and suture 14 are initially located within needle supply station 22. Surgical needle 12 is firmly secured within needle support structure 24 while suture 14 extends through notch 64 and pointed end 18 of surgical needle 12 is protected by shield 28. As noted hereinabove, arms 36 engage second and third portions 40, 42 of surgical needle 12 to hold a first portion 34 of needle 12 securely against notch 32 formed in inflexible support leg 30. As shown, jaw 108 is initially advanced towards the jaw receiving structure 26.

Referring now to FIGS. 8 and 9, as lower jaw 108 is advanced towards jaw receiving structure 26, the lower jaw 108 is positioned between first arm 46 and L-shaped second arm 48. Preferably lips 56 and 58 secure lower jaw 108 between arms 46 and 48. First arm 46 and second art 48 guide lower jaw 108 toward needle 12 in a direction generally orthogonal thereto. Further, it should be noted that angled portion 54 engages a wide portion 134 of lower jaw 108 to limit the advancement of lower jaw 108 into the jaw receiving structure 26. Thus, upon insertion of lower jaw 108 into the jaw receiving structure 26, lower jaw 108 is securely and accurately positioned about suture end 16 of surgical needle 12 proximal to pointed end 18.

Referring now to FIG. 10, release lever 130 is pivoted to a closed or proximal needle clamping position to securely clamp suture end 16 of surgical needle 12 in the manner described hereinabove. At this point, surgical needle 12 is securely clamped within lower jaw 106 of vascular suturing instrument 100 and may be removed by lifting vascular suturing instrument 100 away from base 20 of loading unit 10. Legs 36 are sufficiently flexible to allow surgical needle 12 to be pulled free of needle support structure 24 while first and second arms 46 and 48 are sufficiently flexible to allow lower jaw 106 to snap free of lips 56, 58 on first and second arms 46, 48. Further, as noted hereinabove, inclined surface 44 on inflexible support leg 30 along with inclined surfaces 60, 62 on straight portion 52 and angle portion 54, respectively, allow surgical needle to be lifted clear of needle support structure 24 and jaw receiving structure 26 without damage to, or dislocation of, surgical needle 12. When surgical needle 12 has been lifted clear of needle support structure 24, vascular suturing instrument 100 may continue to be lifted to draw suture 14 off of the suture rail 74. Thus, in this manner a surgical needle 12 having a length of suture 14 attached at a suture end 16 thereof is securely grasped at suture end 16 thereof by vascular suturing instrument 100 and is now ready for use in a surgical suturing operation.

Should the vascular suturing operation require additional surgical needles and associated lengths of suture, loading unit 10 may be rotated to or manipulated to position the second needle supply station 22 in line with vascular suturing instrument 100 and vascular suturing instrument 100 may be reloaded with a new surgical needle 12 and suture 14 in the manner immediately described hereinabove.

It will be understood that various modifications may be made to the embodiments disclosed herein. For example, as noted hereinabove, the disclosed embodiments of the loading unit are suitable for use with various surgical suturing apparatus of the type which surrounds and securely grasps one end of a surgical needle. Additionally, the embodiments may include more than two needle supply stations. Also, the jaw receiving structure may be oriented toward the needle at a direction other than orthogonal thereto. Further, the disclosed embodiments may utilize other forms of suture retaining structure such as, for example, suture reel's, channels, etc. for the storage of sutures attached to the surgical needles. Additionally, as noted hereinabove, the disclosed embodiments may also be modified to accommodate various other needle configurations such as, for example, curved surgical needles. Therefore, the above description should not be construed as limited, but merely exemplifications of preferred embodiments. Those skilled in the art will envision other modifications within the scope and spirit of the claims appended hereto.

What is claimed is:

1. A loading unit for loading a suture comprising:
   a) a base;
   b) first needle support structure on the base for supporting a surgical needle; and
   c) jaw receiving structure on the base for guiding a jaw of a suturing instrument into predetermined alignment with the needle, the jaw receiving structure being configured to frictionally engage the jaw of the surgical instrument such that the jaw is positioned by the jaw receiving structure to orthogonally approach the needle at a portion of the needle proximal to a pointed tip of the needle.

2. The loading unit as recited in claim 1, wherein the jaw receiving structure has a first arm and a second arm spaced from the first arm such that the jaw of the suturing instrument is insertable therebetween.

3. The loading unit as recited in claim 2, wherein the jaw receiving structure is oriented with respect to the needle support structure such that a distal end of the jaw inserted between the first arm and the second arm is positioned about a suture end of the surgical needle.

4. The loading unit as recited in claim 2, wherein the second arm is configured to limit the amount of advancement of the jaw between the first and second arms.

5. The loading unit as recited in claim 4, wherein the second arm has a first portion which is spaced further from the first arm than a second portion of the second arm and configured to engage a wide portion of the jaw.

6. The loading unit as recited in claim 2, wherein the second arm defines a notch for passage of a suture therethrough.

7. The loading unit as recited in claim 2, wherein at least one of the first and second arms has a lip thereon configured to releasably engage the jaw.

8. The loading unit as recited in claim 1, wherein the needle support structure has an inflexible leg configured to engage a first portion of the surgical needle and a first flexible leg configured to engage a second portion of the surgical needle longitudinally offset from the first portion.

9. The loading unit as recited in claim 8, wherein the first flexible leg extends from the base at an obtuse angle to engage the second potion of the needle.

10. The loading unit as recited in claim 8, wherein the needle support structure has a second flexible leg configured to engage a third portion of the surgical needle.

11. The loading unit as recited in claim 1, further comprising a shield on the base, the shield partially surrounding the pointed lip of the surgical needle when the surgical needle is engaged by the needle support structure.

12. The loading unit as recited in claim 1, wherein the base has a top plate and a bottom plate engagable with the top plate to define a cavity therebetween.

13. The loading unit as recited in claim 12, further comprising suture retention structure disposed within the cavity and the top plate has a portion defining an opening communicable with the cavity.

14. The loading unit as recited in claim 13, wherein the suture retaining structure is a rail projecting from a face of the top plate and about which a length of suture attached to the needle may be wound.

15. A loading unit for loading a suture comprising:
   a) a base;
   b) a first needle supply station on the base having first needle support structure and first jaws receiving structure, the first jaw receiving structure orienting a jaw received therein in a first direction orthogonal to a needle; and
   c) a second needle supply station on the base having second needle support structure and second jaw receiving structure, the second jaw receiving structure facing in a direction generally opposite that of the first jaw receiving structure.

16. The loading unit as recited in claim 15, wherein the first jaw receiving structure is proximal of a pointed end of the needle retained on the first needle support structure.

17. A loading unit for loading a suture into a jaw of a surgical suturing apparatus, the loading unit comprising:
   a) a body portion;
   b) a needle releasably supported on the body portion; and
   c) a jaw receiving channel on the body portion and defined by first and second spaced apart wall portions, the first and second wall portions orienting the channel generally orthogonal to the needle and configured to receive a jaw of a suturing instrument therein.

18. The loading unit as recited in claim 17, wherein the jaw receiving channel intersects a portion of the needle proximal of a pointed end of the needle.

19. A loading unit for loading a suture into a jaw of a surgical suturing instrument comprising:

a) a body portion;

b) a needle having a proximal end portion and a distal end portion;

c) needle support structure on the body portion supporting the proximal end portion and the distal end portion of the needle; and d) jaw receiving structure on the body portion for frictionally engaging the jaw of a surgical suturing instrument and configured to guide the jaw relative to the needle so as to engage the needle.

20. The loading unit as recited in claim 19, wherein the jaw receiving structure has a first arm and a second arm spaced from the first arm such that the jaw of the suturing instrument is insertable therebetween.

21. The loading unit as recited in claim 20, wherein at least one of the first and second arms has a lip thereon configured to releasably engage the jaw.

22. The loading unit as recited in claim 19, further comprising a shield on the base, the shield partially surrounding a pointed tip of the needle when the needle is supported on the needle support structure.

23. The loading unit as recited in claim 19, further comprising suture retention structure on the body portion.

24. A method of applying a surgical needle to a suturing instrument comprising the steps of:

a) providing a loading unit having needle support structure releasably engaging a surgical needle and spaced apart arms configured to receive a jaw of a suturing instrument;

b) inserting the jaw of the suturing instrument between the spaced apart arms such that the jaw is releasably engaged by the arms;

c) advancing the jaw within the arms generally perpendicularly toward the surgical needle such that a distal end of a jaw is about an end of the surgical needle;

d) securing the end of the surgical needle within the distal end of the jaw; and e) lifting the surgical needle free of the needle support structure.

* * * * *